United States Patent [19]

Grady et al.

[11] Patent Number: 4,534,051
[45] Date of Patent: Aug. 6, 1985

[54] MASKED SCANNING X-RAY APPARATUS

[75] Inventors: John K. Grady, 300 Foster St., Littleton, Mass. 01460; Richard E. Rice, Arlington, Mass.

[73] Assignee: John K. Grady, Harvard, Mass.

[21] Appl. No.: 453,749

[22] Filed: Dec. 27, 1982

[51] Int. Cl.³ .............................................. H04N 7/18
[52] U.S. Cl. .................... 378/099; 358/111; 378/146
[58] Field of Search .................. 378/146, 99, 7, 19, 378/111, 4

[56] References Cited

U.S. PATENT DOCUMENTS 4,394,738  7/1983  Wagner .................................. 378/4
4,404,591  9/1983  Bonar .................................. 378/146

OTHER PUBLICATIONS

Sorenson et al., "Investigations of Moving Slit Radiography," *Radiology* 120, pp. 705–711, Sep. 1976.

*Primary Examiner*—Alfred E. Smith
*Assistant Examiner*—T. N. Grigsby
*Attorney, Agent, or Firm*—James H. Grover

[57] ABSTRACT

An X-ray system radiates through a subject to an X-ray receptor secondarily emitting a light image includes a moving X-ray mask with X-ray windows between the source and receptor. An electro-optical camera tube views the light image, and the mask includes means for adjusting the width of the windows.

24 Claims, 4 Drawing Figures

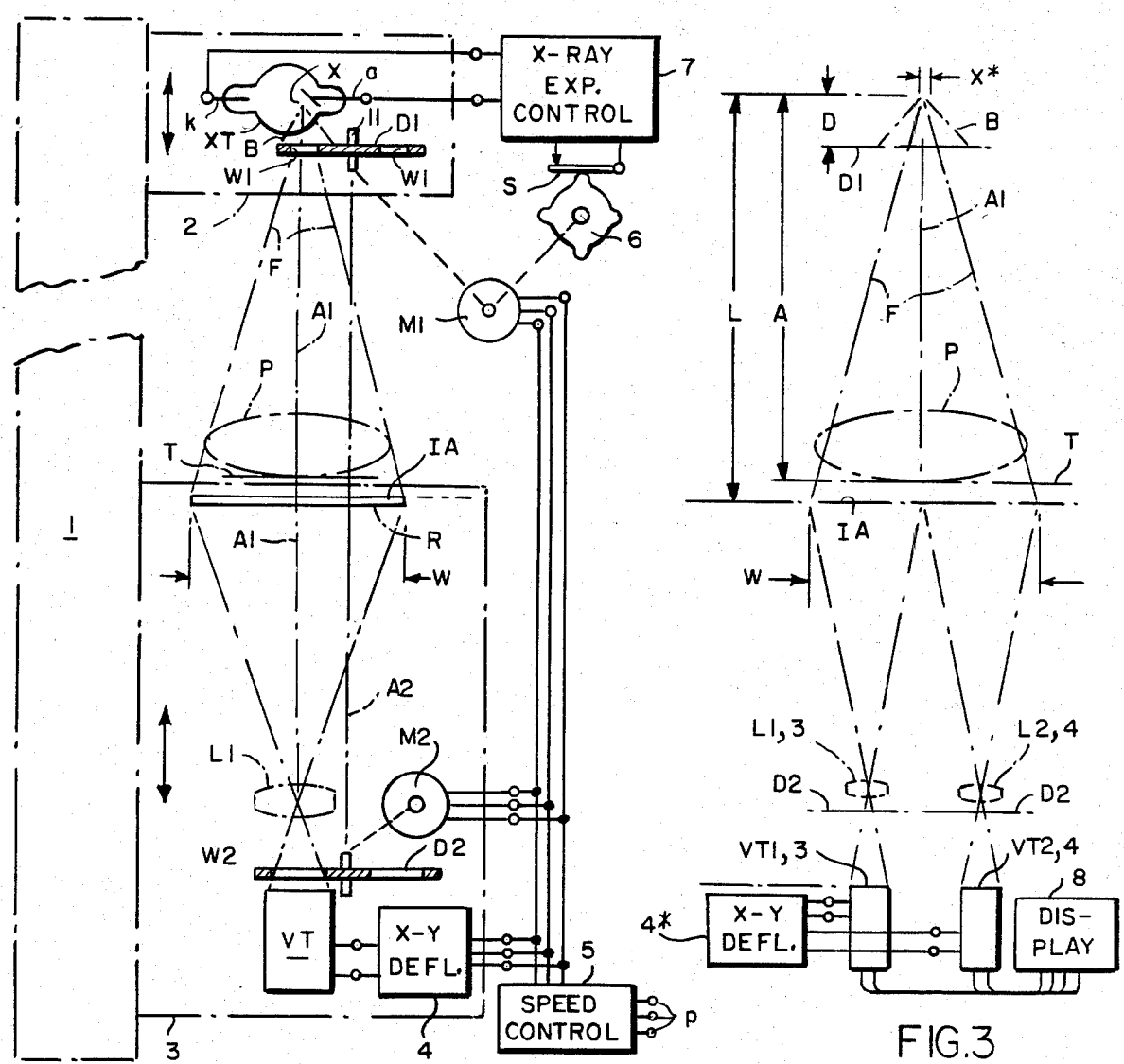
FIG.1
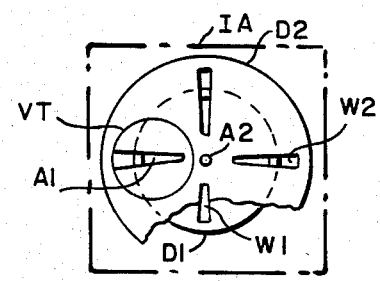
FIG.2
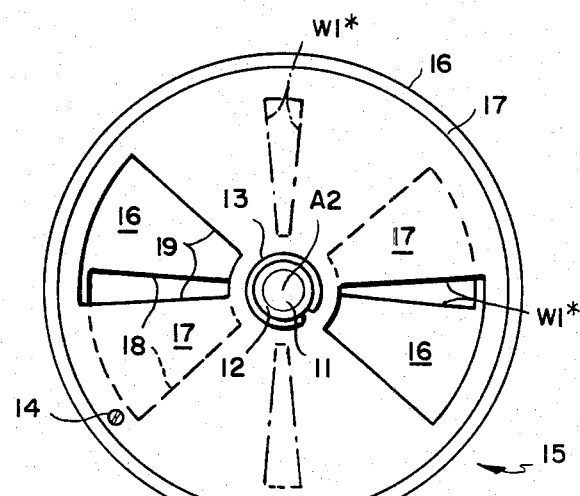
FIG.3
FIG.4

MASKED SCANNING X-RAY APPARATUS

BACKGROUND OF THE INVENTION

The invention relates to X-ray apparatus for radiologically examining a subject in which the beam emitted by an X-ray tube or like source is partially obstructed by a moving X-ray opaque mask, typically a rotating disk with a slit or other X-ray window which transmits a shaped scanning X-ray beam through the subject to a secondary image generating X-ray receptor such as a scintillation screen. As shown in U.S. Pat. Nos. 3,780,291 and 4,315,146, such equipment scans the subject with a nearly one dimensional, fan-shaped, beam rather than the full two dimensional pyramidal or conical beam radiating from the X-ray tube and a second rotating disk, coordinated with the first, masks radiation beyond the subject and therefore reduces the amount of scattered radiation in the image of the receptor. By scattered radiation is meant radiation incident on the X-ray receptor on paths other than directly from the source. Such scattered radiation degrades the contrast of the secondary image produced by direct radiation more or less depending on the fraction of scattered X-radiation relative to the total X-radiation on the receptor. An early form of multiple-masked scanner is shown in French Pat. No. 521,746 issued Mar. 14, 1921 to A. Dauvillier. Such early systems, however, required exposures times so long, 3 to 15 seconds, as to be of little use in modern rapid, multiple exposure X-ray examination of medical subjects.

A rapid sequence of X-ray exposures may be taken with scanning X-ray apparatus by increasing the power applied to the X-ray tube and hence the intensity of its emission. But there is a limit or maximum rated power which may be applied to an X-ray tube, and there is an upper limit to the fraction of scattered radiation which can be permitted without seriously degrading the quality of the secondary image.

Accordingly it is an object of the present invention to minimize the fraction of scattered radiation reaching the X-ray receptor while operating the X-ray tube within its power capacity.

SUMMARY OF THE INVENTION

According to the invention an X-ray system comprises an X-ray beam source of finite size radiating through the position of a radiological subject to an imaging area; an X-ray receptor at the imaging area emitting secondary radiation on receipt of X-rays; moving X-ray mask means between the source and receptor including an X-ray window transmitting a shaped X-ray beam of width scanning across and through the subject position to the receptor to produce a secondary radiation image at the imaging area; and means viewing the imaging area for utilization of the secondary image; wherein the mask means includes means for adjusting the width of the mask window, thereby to minimize the fraction of scattered radiation reaching the X-ray receptor while operating the X-ray tube within its power capacity.

The utilization means comprises electro-optical flying-spot scanner means for viewing the image area and converting the secondary image to corresponding electrical signals. Flying spot scanners include image isocons, image intensifiers, television camera tubes of all types, mechanical facsimile scanners and solid state photoelectric image scanners such as self-scanned photodiode arrays, charge injection devices and charge coupled devices (Fairchild CCD, Palo Alto, Calif.).

Also the present inventions comprise the method of exposing a subject to X-radiation for one or more scans which comprises transmitting the X-radiation through the width of a window of a moving X-ray mask means, thence through the subject to an X-ray receptor; and before transmission adjusting the width of the mask window in the direction of mask movement, thereby to minimize X-ray dosage of the subject while optimizing the effective X-radiation transmitted to the receptor within the capacity of the X-ray source. The mask width can be adjusted between a minimum and a maximum according to mathematical functions which involve the size of the X-ray source, the desired X-ray dosage, the time of transmission of X-rays to the subject, the distance from the source through the subject to the mask means and to the receptor, the width of the receptor, and the amount of radiation desired to be scattered to the receptor.

DRAWING

FIG. 1 is an optical diagram of an X-ray system producing a visible image according to the invention showing structural parts, including a moving mask, schematically.

FIG. 2 is a view along the radiation axis of FIG. 1.

FIG. 3 is an optical diagram of an alternate form of the invention; and

FIG. 4 is an axial view of an adjustable mask.

DESCRIPTION

In the X-ray system of FIGS. 1 and 2 the X-radiation source is the focal spot X on the anode a of an X-ray tube XT. From the source X a pyramidal or conical beam B is radiated on a radiation axis A1 through the position P of a subject such as a human patient on an X-ray transmissive support table T. Beyond the patient position P is an X-ray receptor R having an X-ray responsive imaging area or plane IA of width W. Typically the receptor is a scintillation screen emitting visible secondary radiation on receipt of X-rays, but other known radiation receptors such as film may be used. The secondary radiation image at the area IA is viewed on the axis A1 by electro-optical utilization means including one of the flying spot scanners previously mentioned such as a video camera tube VT, which converts the secondary image into a frame of electrical video signals corresponding to the subject under examination, and a lens system L1 which projects the secondary image onto the light responsive surface at the receiving end of the tube VT. The secondary image may also be projected by fibre optics to a photodiode array.

The X-ray tube XT is mounted in a first carriage 2 capable of reciprocal movement on a main frame 1 toward and away from the patient position P. The receptor R, and electro-optical system, lens L1 and video tube VT, are mounted in a second carriage 3 similarly supported reciprocally on the main frame 1. The patient table T is usually supported independently of the main frame 1 and carriages 2, 3, as shown, for example, in U.S. Pat. No. 3,892,967.

The X-ray beam B is partially intercepted by an X-ray opaque mask comprising a first rotating disk D1 typically having four X-ray transmissive slits or windows W1. As shown in FIG. 2 the windows W1 are sectoral and will transmit a fan-shaped scanning X-ray beam F while the disk D1 masks the remainder of the conical beam B from the receptor R. The windows might, however, be parallel sided rectangular slits in a belt moving linearly or reciprocating through the X-ray beam B. Hereinafter the term "window width" refers to the average width of a sectoral window or the constant width of a rectangular window. A similar but larger rotating disk D2 with four light transmissive windows W2 is located between the lens L1 and video tube VT before the image plane of lens L1. The two disks D1, D2 are rotated on a common axis A2 by synchronous motors M1, M2 respectively. As shown in FIG. 2 the windows W1, W2 of the disks are optically superimposed so that, as the first disk mask D1 is synchronously driven by connection through a speed control 5 to clock regulated alternating current power terminals p, the second disk windows W2 scan the secondary image area IA substantially simultaneously with the scanning of the same area by the first disk windows W1. The X-Y deflection circuit 4 for the video tube scanner is also connected to the synchro control terminals p so that its scan is coordinated with the mask means. With a scintillation screen of very brief image persistence the scan by the video tube is substantially simultaneous with scanning by the masks. But the receptor may include secondary image storage.

The X-ray tube XT is energized by an electronic X-ray exposure control 7 linked through the motor M1 to the power terminals p. For purposes of illustration a mechanical analog of the electronic control is shown. The analog comprises a rotary cam 6 closing a switch S in synchronism with the disk D1 such that the X-ray exposure control 7, in response to closure of the switch S energizes the X-ray tube XT substantially only during the times when the X-ray mask windows W1 are transmissive of X-rays to the image area IA of the receptor and not when the transmitted fan beam is beyond the image area, thus reducing power requirements and scattered X-radiation, and increasing the instantaneous power of the tube.

As shown in FIG. 3 a significant improvement in efficiency of the electro-optical system of lens optics and flying spot scanner can be realized if a plurality of lenses and scanners view discrete and separate areas of the secondary image of the receptor R at the plane IA. Preferably the image area is divided into four quadrants respectively viewed by four electrooptical systems L1, VT1; L2, VT2; L3, VT3; and L4, VT4, the third and fourth of these systems being behind the first and second. The four video tubes are controlled by an X-Y deflection circuit 4* modified to synchronize scan of the respective tubes so that the scan lines effectively join as they pass from one quadrant of the image area to another. The respective outputs of the four scan tubes are supplied to a display 8 such as a cathode ray tube with the same synchronism as the scanning so as to reconstruct the four image quadrants in one continuous display image.

In comparable single and quadruple systems the image area viewed is 35 by 35 centimeters, each lens has an f-number of 1.0, and each video tube VT has a photosensitive surface 10.2 centimeters in diameter. To project the entire image area on the single 10.2 cm. video tube of FIG. 1 using a single lens the diameter of which is 25 cm. requiring a focal length of 25 c.m., and an image area to video tube spacing of 177 cm. In the equivalent quadruple system of FIG. 5 each of the four lenses is 22 cm. in diameter with a focal length of 22 cm. and an image area to video tube spacing of 107 cm. which reduces the optical space requirements almost 40%, while maintaining the same corner to center brightness ratio of 0.95 due to the cosine law.

Although the lens efficiency is increased and the brightness of the receptor image is not increased, an economical benefit is realized because four small lenses are less expensive than an equivalent single large lens.

A most significant aspect of the present invention applicable to all the illustrated embodiments resides in the adjustability of the width of the X-ray transmissive windows W1 in the X-ray mask D1.

Shown in FIG. 4 is a composite disk 15 which preferably is substituted for the first disk D1 of FIGS. 1 and 2. The composite disk 15 comprises two superimposed disks 16 and 17, one disk 16 being secured to the shaft 11 driven by the moter M1 and the one disk 17 having a sleeve 12 rotatably secured on the shaft by a retainer ring 13. While the one disk 17 may be rotated relative to the other disk, the two disks are normally locked to each other by a set screw 14 threaded through one disk 16 and engaging the other against relative movement. The respective disks 16 and 17 each have, for example, four relatively large sectoral windows 18 and 19 which may include an angle from a few degrees to nearly ninety degrees. The windows of both disks overlap to define smaller sectoral X-ray windows W1* opening through both disks and adjustable by relative rotation of the disks 16 and 17.

As the window width is reduced so is the X-ray exposure of the patient, but power to the X-ray tube must then be increased toward its operating limit in order to maintain the required X-ray dose. On the other hand increasing window width increases the flux of randomly scattered X-rays, those rays neither absorbed by the subject nor transmitted linearly, which scattered X-rays falling on the receptor R reduce contrast and resolution and degrade the secondary image on the X-ray receptor. It has been discovered that optimum widths of the window W1, referred to as a minimum width $W_{Min}$ and a maximum width $W_{Max}$ and an acceptable and a preferred range of window widths can be expressed in terms of E, the desired X-ray dosage in milliroentgens; V, the peak or maximum rated voltage in kilovolts applied to the X-ray tube source XT; T the time interval in milliseconds that X-radiation is transmitted to a subject during each scan by a mask window W1; A, the distance in centimeters from the X-radiation source XT through the position of the subject P; D, the distance in centimeters from source XT to the moving mask means D1; W, the width in centimeters of the X-radiation receptor R; L, the distance in centimeters from the X-ray source XT to the receptor R; X*, the size in centimeters of the focal spot on the tube anode a, which is the X-ray source; and F is the allowable fraction of scattered X-rays in milliroentgens selected by the radiologist to fall on the receptor. The distance L is preferably held to between 60 and 200 centimeters. The size of the X-ray source is preferably between 0.03 and 0.2 centimeters. The focal spot is irregular in outline but it is approximately square, and its size may be considered its side dimention. The X-ray source size X* is limited by design of the X-ray tube, but the dimension D may be varied within a range of minimum and maximum widths defined respectively by the approximate expressions:

$$W_{Min} = 5/10,000(E/(12VT - VT \ln T))(A^2DW/LX^*); \quad (1)$$

and $$W_{Max} = F(DW/L). \quad (2)$$

Both expressions are somewhat approximated from computed models, but the approximation is well within useful, and practical limits. E may be varied between the practical limits of 0.25 and 100 milliroentgens; V between 50 and 100 peak kilovolts; and T between 5 and 1500 milliseconds.

At or near minimum value $V_{Min}$ determined by expression (1) the window width is optimum. Further reduction in width below the minimum value $W_{Min}$ exceeds the power capacity of the X-ray tube. Window widths greater than the minimum width are practical at or below the maximum width $W_{Max}$ determined by expression (2). Above maximum width $W_{Max}$ the saving in X-ray tube power diminishes rapidly.

The apparatus described above affords a substantially improved method of procedure for exposing subjects, particularly human patients, to one or more scans of X-radiation. The improved method comprises transmitting X-radiation through the adjustable windows W1* of a moving mask (FIG. 4), thence through the subject to an X-ray receptor, and, prior to exposure adjusting the width of the mask window in the direction of mask movement. The adjustment of the window width may be according to the expressions for minimum and maximum window widths, $W_{Min}$ and $W_{Max}$.

The above described X-ray system and procedural method minimize the total X-ray dosage of the subject and at the same time optimizes the useful radiation transmitted to the radiation receptor while holding voltage applied to the X-ray tube within its peak rating.

It should be understood that the present disclosure is for the purpose of illustration only and that this invention includes all modifications and equivalents which fall within the scope of the appended claims.

I claim:

1. An X-ray system for radiological examination of a subject comprising:
   an X-ray beam source of finite size radiating through the position of a radiological subject to an imaging area;
   an X-ray receptor at the imaging area emitting secondary radiation on receipt of X-rays;
   moving X-ray mask means between the source and receptor including an X-ray window transmitting a shaped X-ray beam of width scanning across and through the subject position to the receptor to produce a secondary radiation image at the imaging area;
   electro-optical means viewing the imaging area for utilization of the secondary image; and
   moving light mask means between the receptor and electro-optical viewing means including a light window transmitting the secondary image;
   wherein the X-ray and light mask means include means for adjusting the width of the mask windows, thereby to minimize the fraction of scattered radiation reaching the X-ray receptor while operating the X-ray tube within its power capacity and to adjust the intensity of the light image transmitted to the electro-optical light viewing means.

2. A system according to claim 1 wherein the distance from the source to the receptor is between 60 and 200 centimeters.

3. A system according to claim 1 wherein the size of the X-ray source is between 0.03 and 0.2 centimeters.

4. A system according to claim 1 wherein the utilization means includes electro-optical means viewing the image area for converting the secondary image to electrical signals corresponding to the subject under examination.

5. A system according to claim 1 wherein the utilization means includes a flying spot scanner with lens means projecting the secondary image on the scanner through the adjustable window of the light mask.

6. A system according to claim 5 wherein the light mask means is between at least a part of the lens means and the scanner, before the image plane of the lens means.

7. A system according to claim 1 wherein the second mask means is closely adjacent the scanner.

8. A system according to claim 1 including control means to synchronize movement of the first said and second mask means for substantially simultaneous transmission of X-rays and secondary radiation through respective windows of the masks.

9. A system according to claim 8 wherein the control means includes means limiting energization of the X-ray source substantially only to times when the first said mask means windows are transmissive to the receptor.

10. A system according to claim 1 wherein the receptor includes means for storing the secondary radiation image.

11. A system according to claim 1 including an X-ray transmissive support wherein the subject position is between the X-ray source and the support.

12. A system according to claim 11 wherein the radiation receptor is located between the support and the utilization means.

13. A system according to claim 1 wherein the viewing means is a flying spot scanner coordinated with the movement at the X-ray mask means.

14. A system according to claim 1 wherein the mask means moves continuously on an orbital path so that the window repeatedly scans the subject position to produce a series of secondary images, and wherein the electro-optical means includes means for converting the secondary images into corresponding series of video signals.

15. The method of exposing a subject to X-radiation for one or more scans which comprises:
   transmitting the X-radiation from a source through the width of a window in a moving X-ray mask means, thence through the subject to an X-ray receptor; and before transmission
   adjusting the width of the mask window in the direction of mask movement, thereby to minimize X-ray dosage of the subject while optimizing the effective X-radiation transmitted to the receptor within the capacity of the X-ray source;
   wherein a mininum window width is selected by adjustment according to the expression:

$$5/10000(E/(12VT - VT \ln T))(A^2DW/LX^*);$$

wherein E is the desired X-ray dosage in milliroentgens, V is the X-radiation source peak voltage, T is the time the X-radiation is transmitted to a subject in each scan, A is the distance from the source through the subject, D is the distance from the X-radiation source to the mask means, W is the width of the receptor, L is the distance from the source to the receptor, and X* is the size of the radiation source.

16. The method according to claim 15 wherein E is varied between 0.25 and 100 milliroentgens.

17. The method according to claim 15 wherein V is varied between 50 and 150 peak kilovolts.

18. The method according to claim 15 wherein T is varied between 5 and 1500 milliseconds.

19. The method according to claim 15 wherein the distance L is varied between 60 and 200 centimeters.

20. The method according to claim 15 wherein the size X* of the X-ray source is between 0.03 and 0.2 centimeters.

21. The method of exposing a subject to X-radiation for one or more scans which comprises:
   transmitting the X-radiation from a source through the width of a window in a moving X-ray mask means, thence through the subject to an X-ray receptor; and before transmission
   adjusting the width of the mask window in the direction of mask movement, thereby to minimize X-ray dosage of the subject while optimizing the effective X-radiation transmitted to the receptor within the capacity of the X-ray source;
wherein a maximum window width is selected by adjustment according to the expression:

$$F(DW/L);$$

wherein F is the selected fraction of X-radiation scattered to the detector, D is the distance from the source to the mask means, W is the width of the receptor and L is the distance from the source to the receptor.

22. An X-ray system for radiological examination of a subject comprising:
   an X-ray beam source of finite size radiating through the position of a radiological subject of an imaging area;
   an X-ray receptor at the imaging area emitting the secondary radiation on receipt of X-rays;
   moving X-ray mask means between the source and receptor including an X-ray window transmitting a shaped X-ray beam of narrow width scanning across and through the subject position to the receptor to produce a secondary radiation image at the imaging area; and
   means viewing the imaging area for utilizing the secondary image;
   wherein the mask window has a minimum width $W_{Min}$ in the direction of mask movement defined by the expression:

$$5/10{,}000(E/(12VT - VT \ln T))(A^2 DW/LX^*);$$

wherein E is the desired X-ray dosage in milliroentgens, V is the X-radiation source peak voltage, T is the time the X-radiation is transmitted to a subject in each scan, A is the distance from the source through the subject, D is the distance from the X-radiation source to the mask means, W is the width of the receptor, L is the distance from the source to the receptor, and X* is the size of the radiation source.

23. An X-ray system for radiological examination of a subject comprising:
   an X-ray beam source of finite size radiating through the position of a radiological subject to an imaging area;
   an X-ray receptor at the imaging area emitting secondary radiation on receipt of X-rays;
   moving X-ray mask means between the source and receptor including an X-ray window transmitting a shaped X-ray beam of narrow width scanning across and through the subject position to the receptor to produce a secondary radiation image at the imaging area; and
   means viewing the imaging area for utilizing the secondary image;
   wherein the mask window has a maximum width $M_{Max}$ in the direction of mask movement defined by the expression:

$$F(DW/L);$$

wherein F is the selected fraction of X-radiation scattered to the detector, D is the distance from the source to the mask means, W is the width of the receptor and L is the distance from the source to the receptor.

24. An X-ray system for radiological examination of a subject comprising:
   an X-ray beam source of finite size radiating through the position of a radiological subject to an imaging area;
   an X-ray receptor at the imaging area emitting secondary radiation on receipt of X-rays;
   moving X-ray mask means between the source and receptor including an X-ray window transmitting a shaped X-ray beam of narrow width scanning across and through the subject position to the receptor to produce a secondary radiation image at the imaging area; and
   means viewing the imaging area for utilizing the secondary image;
   wherein the mask window has a width in the direction of mask movement in the range between a minimum $W_{Min}$ and maximum $W_{Max}$ respectively defined by the expressions:

$$W_{Min} = 5/10000(E/(12VT - VT \ln T))(A^2 DW/LX^*);$$

and $$W_{Max} = F(DW/L);$$

wherein E is the desired X-ray dosage in milliroentgens, V is the X-radiation source peak voltage, T is the time the X-radiation is transmitted to a subject in each scan, A is the distance from the source through the subject, D is the distance from the X-radiation source to the mask means, W is the width of the receptor, L is the distance from the source to the receptor, and F is the selected fraction of X-radiation scattered to the detector.

* * * * *